United States Patent [19]

Burzio et al.

[11] Patent Number: 5,401,435
[45] Date of Patent: Mar. 28, 1995

[54] PROCESS FOR INCREASING THE BLEACHING EFFICIENCY OF AN INORGANIC PERSALT OR OF HYDROGEN PEROXIDE

[75] Inventors: Fulvio Burzio, Milan, Italy; Roland Beck, Brussels; Myriam Elsevier, Kampenhout, both of Belgium; Julio Mentech, Lyons, France

[73] Assignee: Ausimont S.p.A., Milan, Italy

[21] Appl. No.: 896,140

[22] Filed: Jun. 9, 1992

[30] Foreign Application Priority Data

Jun. 10, 1991 [EP] European Pat. Off. ............ 91305210

[51] Int. Cl.$^6$ .................. C09K 3/00; C11D 3/395
[52] U.S. Cl. .................. 252/186.38; 252/95; 252/186.39
[58] Field of Search .................. 252/186.38, 186.39, 252/95

[56] References Cited

U.S. PATENT DOCUMENTS

| | | | |
|---|---|---|---|
| 2,955,905 | 10/1960 | Davis et al. | 8/111 |
| 3,477,849 | 11/1969 | Becker | 96/29 |
| 3,723,506 | 3/1973 | Desiongchamps | 206/484 R |
| 3,901,819 | 8/1975 | Nakagawa et al. | 252/186.38 |
| 4,110,242 | 8/1979 | Hase et al. | 252/186.38 |
| 4,800,038 | 1/1989 | Broze et al. | 252/187.17 |

FOREIGN PATENT DOCUMENTS

| | | |
|---|---|---|
| 3821417 | 6/1988 | Germany . |
| 46028226 | 6/1989 | Japan . |
| PCT/DK90/-00022 | 7/1990 | WIPO . |

OTHER PUBLICATIONS

D. Horton et al, "Diazo Derivatives of Sugars, Synthesis of Methyl 2-deoxy-2-diazo-D-arabino-hexonate, its Behavior on Photolysis and Thermolysis and Conversion Into a Pyrazole Derivative", Carbohydrate Research vol. 22, 1972, pp. 151–162.
A. M. Demsey et al, "The Transformation of D-glucono-1,5-lactone Into Ethyl 2,3,4,6-tetra-O-acetyl-D-gluconate and an Ethyl 2,3,4,5-tetra-O-acetyl-6-chloro-6-deoxyhexonate", Carbohydrate Research vol. 16, 1971, pp. 449–451.
H. Takahashi et al, "Reaction of Amino Acids With D-Glycosyl-and D-Gluconyl Isothiocyanates", Chem. Pharm. Bull. vol. 27, No. 5, 1979, pp. 1137–1142.
H. Kuzuhara et al, "Synthesis With Partially Benzylated Sugars. VIII. Substitution At C-5 in an Aldose. The Synthesis of 5-O-Methyl-D-glucofuranose Derivatives", Journal of Organic Chemistry vol. 32, No. 8, Aug. 1967, pp. 2531–2534.
R. Blattner et al, "Photo-bromination of Carbohydrate Derivatives. Part 2. Penta-O-acetyl-beta-D-glucopyranose; The 5-Bromo-derivative and Products of Further Bromination", Journal of the Chemical Society Perkin Transactions I, vol. 7, 1980, pp. 1523–1527.
W. J. Humphlett, "Synthesis of Some Esters and Lactones of Aldonic Acids", Carbohydrate Research vol. 4, 1967, pp. 157–164.
J. Lehrfeld et al, "Gas Chromatographic Analysis of Mixtures Containing Aldonic Acids, Alditols, and Glucose", Analytical Chemistry vol. 56, Sep. 1984, pp. 1803–1806.
Chemical Abstracts vol. 102, No. 13, 1 Apr. 1985, p. 752, abstract No. 113874f, which is an English language abstrat of Japanese Patent 59,136,488.

*Primary Examiner*—Robert L. Stoll
*Assistant Examiner*—Joseph D. Anthony
*Attorney, Agent, or Firm*—Bryan Cave

[57] ABSTRACT

A process for increasing the bleaching efficiency of an inorganic persalt or hydrogen peroxide by adding to said persalt or $H_2O_2$ an activating agent. The activating agent is an acetylated gluconic acid derivative, such as N-methyl-N-acetyl pentaacetyl gluconamide, N-methyl-N-acetyl pentaacetyl gluconamide or tetraacetyl gluconolactone. The invention also relates to the acetylated gluconic acid derivatives themselves.

8 Claims, No Drawings

PROCESS FOR INCREASING THE BLEACHING EFFICIENCY OF AN INORGANIC PERSALT OR OF HYDROGEN PEROXIDE

The invention relates to a process for increasing the bleaching efficiency of an inorganic persalt or hydrogen peroxide and to bleaching and/or detergent compositions suitable for removing stains from textiles or from other products such as paper, cellulose, cork, hair etc.. The inorganic persalts to which the composition of the present invention can be applied are substances capable of releasing hydrogen peroxide in an aceteous solution. Examples of such inorganic persalts are alkali metal percarbonates, persulfates, persilicates, perpyrophoshates and their mixtures. Preferred alkali metals are Na, K and Li, particularly Na.

When an inorganic persalt is used alone its provide a satisfactory bleaching effect at the boil, but at a lower temperature, such as at 40° C. or 60° C., where the washing machines operate, its bleaching efficiency is extremely low.

Due to the trend of lowering the washing temperature and of energy saving as well as to the diffused use of synthetic and coloured fabrics, bleaching activators have been developed which improve the bleaching efficiency of inorganic persalts.

Among the known bleaching activators the TAED (tetraacetyl-ethylenediamine) is the most efficacious one, which increases at a high extend the bleaching activity of inorganic persalts (peroxide). However, the TAED being a compound directly or indirectly derived from oil, has the disadvantage of contaminating the environment.

U.S. Pat. No. 2,955,905 describes a bleaching composition containing an inorganic persalt together with an organic carboxylic ester which acts as a bleaching activator. Examples of esters are among others esters of polyhydric aliphatic alcohols such as mannitol-hexaacetate, sorbitol hexa-acetate, and esters of mono- and -disaccharides such as fructose-penta-acetate, glucose-penta-acetate, glucose-tetra-acetate and sucrose-octaacetate.

These organic carboxylic esters do not pollute the environment and, in some conditions, expose acceptable improvement in the bleaching activity of inorganic persalts; however, test results carried out by the Applicant show that the bleaching activity of inorganic persalts cannot be significantly improved by increasing the ratio by weight of said organic carboxylic esters to the inorganic persalts. This property of said carboxylic esters does not make them attractive, since the aim is to always improve the bleaching.

Thus, object of the present invention is to provide a process for increasing the bleaching activity of inorganic persalts by adding to said persalts a bleaching activator which is lack of the above-cited disadvantegous properties.

The Applicant has now surprisingly found that some acetylated gluconic acid derivatives deriving from natural, renewable substances, are endowed with those above-reported properties not possessed by TAED or the acetylated carbohydrates of U.S. Pat. No. 2,955,905. Therefore, they forming a new class of bleaching activators, are suitable to be used as such for inorganic persalts or hydrogen peroxide.

According to the present invention a process is provided for increasing the bleaching efficiency of an inorganic persalt or hydrogen peroxide, e.g. sodium perborate, mono-or tetra-hydrate, wherein an acetylated gluconic acid derivative is added to said inorganic persalt or hydrogen peroxide; the gluconic acid derivative has the formula (I) or (II):

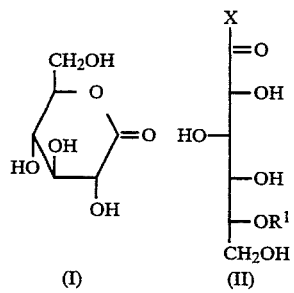

wherein X is

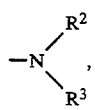

—$OR^4$, where $R^2$ and $R^3$ may have the same or different meaning, and are H, alkyl having from 1 to 5 carbon atoms, alylcarbonyl having from 1 to 3 carbon atoms, hydroxyalkyl having from 1 to 5 carbon atoms and carboxyalkyl having from 1 to 5 carbon atoms and from 1 to 3, preferably from 1 to 2 carboxyl groups, with the proviso that when $R^2$ is H, $R^3$ is different from H; $R^4$ is an alkyl group having from 1 to 5 carbon atoms; and $R^1$ is H or alkylcarbonyl having from 1 to 3 carbon atoms.

Among the preferred compounds are those having formula (II) wherein X is

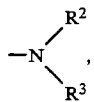

and where $R^1$, $R^2$ and $R^3$ are characterized hereinbefore.

Examples of acetylated gluconic acid derivatives are N-methyl pentaacetyl gluconamide, N-methyl-N-acetyl pentaacetyl gluconamide, tetraacetyl gluconolactone, N-hydroxyethyl tetraacetyl gluconamide, N-succinyl tetraacetyl gluconamide and N-carboxymethyl pentaacetyl gluconamide.

The average O-acetylation degree of said acetylated gluconic acid derivatives is from 2 to 5, preferably from 3 to 5 and most preferably from 4 to 5.

When also the X group is acetylated in the compounds having formula (II), the total acetylation degree is from 2 to 6, preferably from 3 to 6 and most preferably from 4 to 6.

The acetylated gluconic acid derivatives according to the invention, hereinafter referred to as GAD, can be prepared, according to well known methods, either by direct acetylation of the gluconolactone having formula (I) followed by the introduction of X groups or via acetylation of the compounds having formula (II).

The GADs according to the present invention show, contrary to other acetylated carbohydrate derivatives, a bleaching efficiency equal to or even higher than the best known activating agent, i.e. the TAED (tetraacetyl-ethylenediamine). The GADs according to the present invention show the advantage with respect to TAED that they are recovered from natural, renewable substances and not from compounds directly or indirectly derived from oil. Therefore, GADs contribute to the protection of the environment.

The higher the amount of GADs (up to the stoichiometric ratio with the persalt or hydrogen peroxide), the higher the bleaching efficiency of the activating agent. Such property, common with the TAED, makes the GADs particularly suitable for satisfying the requirement of using higher amount of activating agents in the bleaching and/or detergent compositions, aiming to an always increasing bleaching.

GADs may be directly added as such to a composition containing the persalt or it can be previously admixed with the persalt used in the bleaching process. In the case of granular compositions, GAD may be added in granular form, showing suitable mechanical features and suitable granulometric distribution. The bleaching and/or detergent compositions containing GAD and persalt may also contain other usual components, such as anionic, non-ionic or amphoteric surfactants, alkali metal salts (e.g. sodium carbonate, sodium tripolyphosphate), neutral salts (e.g. sodium sulphate), zeolites, carboxymethyl cellulose, perfumes, enzymes etc..

The molar ratio between the bleaching activator and the persalt or hydrogen peroxide usually is from 10:90 to 50:50. When the bleaching efficiency of a persalt or hydrogen peroxide is exploited at a low temperature and for a short time, the molar ratio of GAD to persalt or hydrogen peroxide should preferably be increased.

The following examples are provided for merely illustrative purpose and do not limit in any way the scope of the invention.

GAD of example 1 hereinafter referred to as GAD-1, having the structure corresponding to N-methyl pentaacetyl gluconamide, was prepared as follows:

A suspension of 50 g gluconolactone in 500 ml of isopropanol/methanol (4/1) was treated with 23.8 ml of a 40% N-methylamine solution for 30 minutes. The N-methylgluconamide obtained in quantitative yields, was treated at 60° C. with 69 ml acetic anhydride and 35 ml acetic acid in the presence of 1% concentrated sulphuric acid.

GAD of examples 4-6, hereinafter referred to as GAD-2, having the structure corresponding to N-methyl N-acetyl penta acetyl gluconamide, was synthetized by following the procedure of the preparation of GAD-1, however, during the acetylation step the amount of sulphuric acid was increased to 10% to obtain addionally N-acetylation.

GAD of example 7-9, hereinafter referred to as GAD-3, having the structure corresponding to tetra acetyl gluconolactone, was prepared in a classical acetylation procedure at 60°-100° C.

GAD of examples 10-12, hereinafter referred to as GAD-4, having the structure corresponding to N-acetyl N-succinyl penta acetyl gluconamide, was prepared by acetylation of N-succinyl gluconamide.

GAD of examples 13-15, hereinafter referred to as GAD-5, having the structure corresponding to N-carboxymethyl penta acetyl gluconamide, was prepared by amidation of gluconolactone with glycine followed by acetylation.

Further GAD can be prepared by known processes, e.g. N-succinyl tetra acetyl gluconamide can be obtained by amidation of GAD-3, i.e. tetra acetyl gluconolactone, with L-aspartic acid; N-hydroxyethyl tetraacetyl gluconamide can be prepared by amidation of GAD-3 with ethanolamine.

EXAMPLE 1

An automatic washing machine (IGNIS) was made to run under the following conditions:
washing program at 60° C.;
linen load: 3 kg of cotton swatch (white and clean) per washing cycle;
6 g/washing cycle of GAD-1, corresponding to 4% bleaching activator in the detergent, as reported in Table 1, were added to the following detergent composition (which was also used in all the other examples):

| | |
|---|---|
| sodium perborate tetrahydrate: | 30 g/washing |
| detergent base (phosphorous-free, free of bleaching agents) | 114 g/washing. |

| Said detergent base contained: | (%) w/w |
|---|---|
| overall surfactants (linear sodium dodecylbenzene sulphonate + soap + $C_{13}$-$C_{15}$ alcohol, ethoxylated with 7 EO) | 15.4 |
| zeolite (4Å) | 28.6 |
| sodium silicate ($SiO_2$/$Na_2O$=2) | 4.4 |
| sodium carbonate | 16.5 |
| sodium sulfate | 26.5 |
| carboxymethyl cellulose | 1.2 |
| antiincrustation copolymers | 4.8 |
| optical bleaching agents | 0.3 |
| water up to | 100.0 |

For the determination of the bleaching efficiency (bleaching booster activity) the clean linen was washed together with 2 samples (swatches)/washing cycle, previously stained in a standard way, with red wine, according to the test of the European Institute of Sankt Gallen (EMPA 114). At the end of each washing cycle said 2 samples were dried and ironed; the whiteness degree was then measured by means of an Elrepho-Zeiss reflectometer. The resulting bleaching percentage (measure of the bleaching efficiency), reported in Table 1, was determined by the formula:

$$\text{bleaching (\%)} = (A-B)/(C-B) \times 100$$

where:
A = whiteness degree of the swatch after the washing;
B = whiteness degree of the swatch before the washing;
C = whiteness degree of the swatch completely bleached.

The whiteness degree of the swatches is expressed as percentage of the whiteness degree of MgO, as standard, when measured with a filter No. 6 (wavelength = 464 nm). The thus obtained percentage (71.2%) is reported in Table 1, along with the results of the other examples.

EXAMPLES 2-3

Example 1 was repeated by respectively increasing the amount of activator GAD-1 to 12 and 18 g/washing cycle, corresponding to 8 and 12% in the detergent, respectively. The obtained results are reported in Table 1.

EXAMPLES 4-6

Examples 1-3 were repeated with the difference that GAD-2 (N-acetyl N-methyl penta acetyl gluconamide) was used instead of GAD-1. The results obtained are reported in Table 1.

EXAMPLES 7-9

Examples 1-3 were repeated with the difference that GAD-3 (tetra acetyl gluconolactone) was used instead of GAD-1. The results obtained are reported in Table 1.

EXAMPLES 10-12

Examples 1-3 were repeated with the difference that GAD-4 (N-succinyl tetraacetyl gluconamide) was used instead of GAD-1. The results obtained are reported in Table 1.

EXAMPLES 13-15

Examples 1-3 were repeated with the difference that GAD-5 (N-carboxymethyl penta acetyl gluconamide) was used instead of GAD-1. The results obtained are reported in Table 1.

EXAMPLES 16-24 (Comparative examples)

Examples 1-3 were repeated with the difference that TAED or octa acetyl sucrose or hexa acetyl sorbitol was used instead of GAD-1. The results obtained are reported in Table 1.

EXAMPLE 25 (Comparative example)

Example 1 was repeated with the difference that the sodium perborate tetrahydrate was used alone in the absence of any bleaching activator. The result obtained is reported in Table 1.

TABLE 1

| Activator | Activator amount (g/washing) | | |
|---|---|---|---|
| | 6 (4%) | 12 (8%) | 18 (12%) |
| | Bleaching % | | |
| GAD-1 (Ex. 1-3) | 71.2 | 73.0 | 77.3 |
| GAD-2 (Ex. 4-6) | 72.4 | 75.3 | 77.7 |
| GAD-3 (Ex. 7-9) | 67.3 | 69.3 | 70.3 |
| GAD-4 (Ex. 1-12) | 65.3 | 66.8 | 69.5 |
| GAD-5 (Ex. 13-15) | 60.1 | 67.8 | 69.8 |
| Comparative tests | | | |
| TAED | 69.7 | 73.9 | 78.0 |
| octa acetyl sucrose | 64.2 | 65.4 | 67.0 |
| hexa acetyl sorbitol | 63.7 | 65.8 | 68.0 |
| NO ACTIVATOR (blank) | 54.9 | | |

We claim:

1. A process for increasing the bleaching efficiency of an inorganic persalt or hydrogen peroxide, said process comprising adding an activating agent to said inorganic persalt or hydrogen peroxide in an amount such that the molar ratio of the activating agent to the persalt or hydrogen peroxide is from 10:90 to 50:50, said activating agent having the formula:

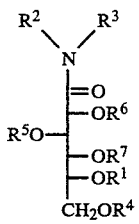

wherein $R^2$ and $R^3$ are the same or different, and are selected from the group consisting of H, alkyl having from 1 to 5 carbon atoms, alkylcarbonyl having from 1 to 3 carbon atoms, hydroxyalkyl having from 1 to 5 carbon atoms, and carboxyalkyl having from 1 to 5 carbon atoms and from 1 to 3 carboxyl groups, with the proviso that when $R^2$ is H, $R^3$ is different from H; $R^1$ is H or alkylcarbonyl having from 1 to 3 carbon atoms; and $R^4$, $R^5$, $R^6$ and $R^7$ are the same or different from each other, and are selected from the group consisting of H and

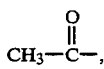

with the proviso that at least one of $R^4$, $R^5$, $R^6$ and $R^7$ is

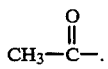

2. Process according to claim 1, wherein the activating agent has a total acetylation degree of from 2 to 6.

3. Process according to claim 1, wherein the activating agent has a total acetylation degree of from 4 to 6.

4. Process according to claim 1, wherein the activating agent is N-methyl-pentaacetyl gluconamide.

5. Process according to claim 1, wherein the activating agent is N-methyl-N-acetylpentaacetyl gluconamide.

6. Process according to claim 1, wherein the inorganic persalt is selected from the group consisting of sodium perborate monohydrate, sodium perborate tetrahydrate and mixtures thereof.

7. Bleaching compositions comprising an inorganic persalt or hydrogen peroxide and the activating agent of claim 1, said activating agent and inorganic persalt or hydrogen peroxide being in a molar ratio of from 10:90 to 50:50.

8. Detergent compositions comprising:
(a) a surfactant;
(b) an inorganic persalt or hydrogen peroxide; and
(c) the activating agent of claim 1, said activating agent and inorganic persalt or hydrogen peroxide being in a molar ratio of from 10:90 to 50:50.

* * * * *

UNITED STATES PATENT AND TRADEMARK OFFICE
CERTIFICATE OF CORRECTION

PATENT NO. : 5,401,435

DATED : March 28, 1995

INVENTOR(S): Fulvio Burzio et al

It is certified that error appears in the above-identified patent and that said Letters Patent is hereby corrected as shown below:

Title Page, item [75] Inventors: "Myriam Elsevier" should read --Myriam Elseviers--.

Signed and Sealed this

Sixth Day of June, 1995

*Attest:*

BRUCE LEHMAN

*Attesting Officer*     *Commissioner of Patents and Trademarks*